United States Patent [19]

Sokol et al.

[11] 4,064,500
[45] Dec. 20, 1977

[54] STRAIN DETECTION APPARATUS AND METHOD FOR RADIOLOGICAL EQUIPMENT

[75] Inventors: Henry R. Sokol, Broadview Heights; Jack R. Sorwick, Novelty, both of Ohio

[73] Assignee: Picker Corporation, Cleveland, Ohio

[21] Appl. No.: 668,623

[22] Filed: Mar. 19, 1976

[51] Int. Cl.² .............................................. G08B 21/00
[52] U.S. Cl. ................................. 340/267 R; 250/446; 340/272
[58] Field of Search ............... 340/272, 267 R, 267 C; 250/416, 450, 449, 448, 447, 446

[56] References Cited

U.S. PATENT DOCUMENTS

| | | | |
|---|---|---|---|
| 2,845,503 | 7/1958 | Durand | 340/267 R |
| 3,265,220 | 8/1966 | Knight | 340/267 C |
| 3,802,379 | 4/1974 | Sandberg | 340/272 |
| 3,916,203 | 10/1975 | Norgren | 250/439 |
| 3,918,301 | 11/1975 | Baer | 340/272 |

Primary Examiner—Glen R. Swann, III
Attorney, Agent, or Firm—Watts, Hoffmann, Fisher & Heinke Co.

[57] ABSTRACT

Apparatus and method are disclosed for detecting excess strain or failure in a main cable interconnecting a movable tower and counterweight assembly in a tiltable X-ray table. A secondary cable, substantially parallel to the main cable, is provided for supplementing the force exerted by the main cable structure between the tower and counterweight to a degree which is a function of the amount of strain occurring in the main cable. Changes in the amount of supplemental force provided by the secondary cable are sensed and used to produce an indication of the main cable strain. A supplemental force indication is accomplished by structure for holding a portion of the secondary cable in a transversely deflected position and by a spring actuated limit switch coupled to the deflected portion. The limit switch produces an indication in response to forces transverse to the length of the secondary cable exerted in the deflected portion, which forces result from increased tension on the secondary cable. The strain indication constitutes an audible signal produced by an audible signal generator in response to actuation of the limit switch.

The X-ray table has a top pivotable through the horizontal, and circuitry and apparatus for preventing further pivoting of the table top when the top has been moved to its horizontal position following the production of a strain indication.

14 Claims, 8 Drawing Figures

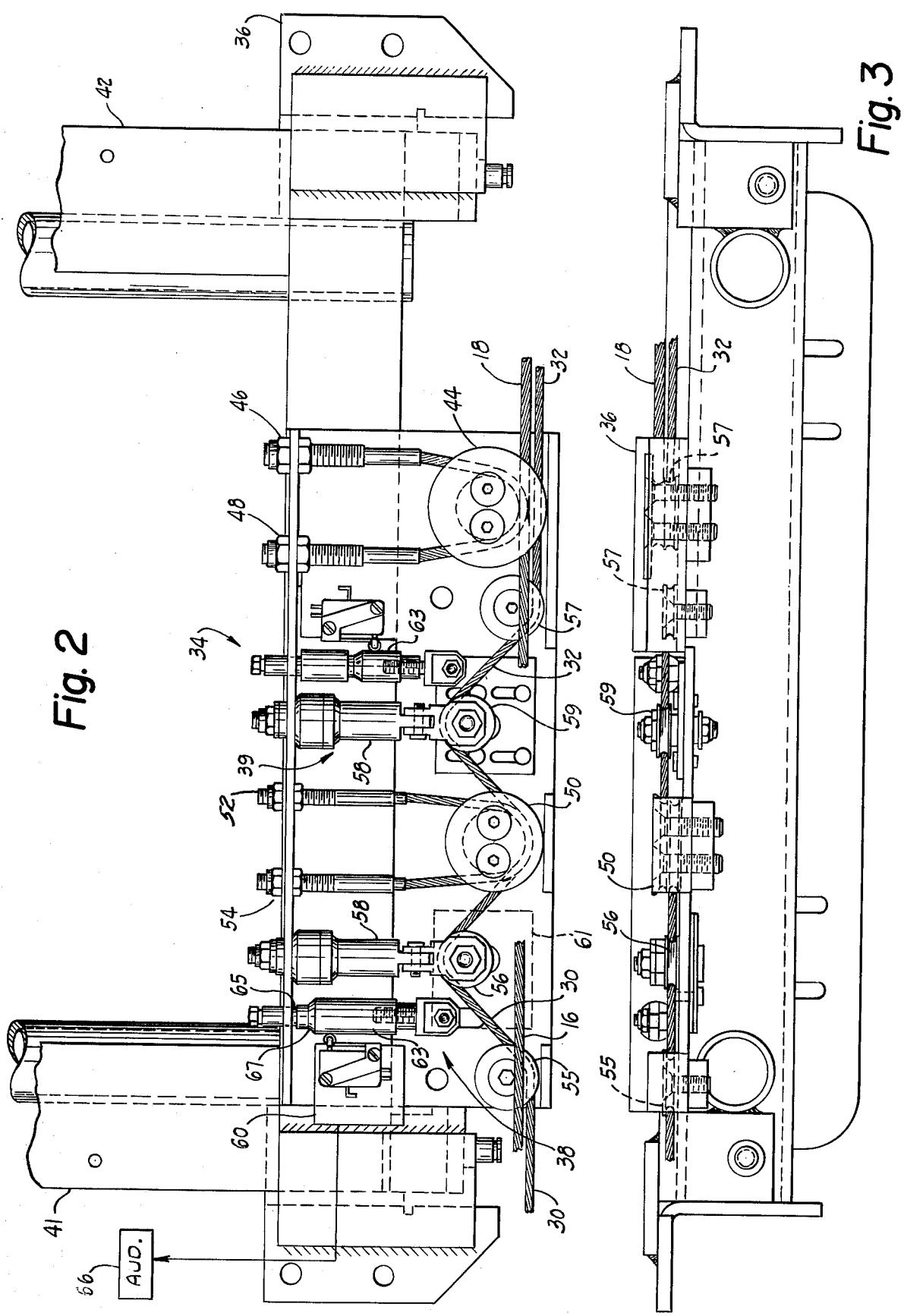

STRAIN DETECTION APPARATUS AND METHOD FOR RADIOLOGICAL EQUIPMENT

RELATED APPLICATIONS AND PATENTS

1. Barrett, et al., U.S. Pat. No. 3,173,008, issued Mar. 9, 1975, under the title "Spot Filmer."
2. R. C. Schiring, et al., U.S. Pat. No. 2,872,584, issued Feb. 3, 1959 under the title "X-ray Apparatus."
3. R. C. Schiring, U.S. Pat. No. 2,997,585, issued Aug. 22, 1961 under the title "Combined Image Amplifier and Fluoroscopic Screen Above X-ray Examination Table."
4. U.S. Pat. No. 3,916,203, filed Sept. 23, 1974, by E. A. Norgren, under the title "X-ray Apparatus Including Counterbalancing Mechanism for Spot Filmer or the Like."
5. A concurrently filed patent application Ser. No. 668,624, for "X-ray Table Lockout Apparatus and Method," by Ronald E. Lutz, et al.

BACKGROUND OF THE INVENTION

Field of the Invention

This invention is directed to X-ray apparatus, and more particularly, to improvement in an X-ray table tiltable about a pivot. The table has an imaging device (a spot filmer or the like) mounted on a tower. The tower is movably attached to the table. The table includes a mechanism for counterbalancing the mass of the tower when the table is tilted.

DESCRIPTION OF THE PRIOR ART

In X-ray examination apparatus, it is known to provide radiological systems including a so-called 90—90 X-ray table in which a table body and its asssociated top are tiltable on a pedestal about an axis transverse to the table length. Such tables are tiltable in either direction 90° from a position in which the table top is horizontal. Thus, the body of the table may be moved clockwise or counterclockwise from the horizontal until its top is vertical, or to any position between the vertical positions. Drive structure, including a reversible electric motor and circuitry to control it, is provided for effecting the desired tilting motion. One such table is that described and claimed in the referenced Schiring, et al., U.S. Pat. No. 2,872,584.

Other tables with lesser degrees of tiltability are also known. Some tables, for example, have a body which is tiltable in one direction from a top-horizontal position to a vertical position, and tiltable in the other direction to a so-called "Trendelenburg" position wherein the angle of the table is approximately 15° from the horizontal.

In most tiltable tables, a guide track is provided parallelling longitudinally the table top. A movable column or tower is slidably mounted on the guide track for movement on a path of travel which is longitudinal with respect to the table top. The column is also mounted for reciprocable rectilinear movement along a guide path transverse to the table top and normal to the column travel along the guide track.

The column supports an X-ray tube which is positioned beneath the table top and within the table body. One or more image producing X-ray responsive devices such as a spot filmer or an image intensification device are supported by a carriage, which is reciprocably mounted on the column for travel along a rectilinear path perpendicular to the plane of the table top.

These three paths of travel permit the carriage to be moved to any selected position over the table top and to any selected distance from the top within the limits of the respective paths of travel.

Since the motion of the column along the guide track has a vertical component when the table top is in a nonhorizontal position, at least one counterweight is used to counterbalance the column. The counterweight is desirable in preventing the heavy tower from tending to slide toward the lowered end of the X-ray table when tilted.

It is known to provide mechanical linkage between the tower and the counterweight to effect automatic counterbalancing of the weight of the tower as the tower is moved along the guide track, so that the table is always in a substantially balanced condition about its pivot on its pedestal.

According to one system, the counterweight is slidably mounted for longitudinal movement parallel to the guide track within the body of the table along a counterweight track. The counterweight and the tower (each weighing about 600 pounds) are connected together by two main or primary connectors made of suitable woven wire cable having an outside diameter of about 3/16 inch.

The cable portions are connected between the counterweight and the tower by way of their engagement with pulleys located at and within opposite ends of the table body. One portion of the cable is connected to one side of the counterweight, and extends outwardly around the pulley at one end of the table, and then inwardly to a point at which it is attached to the tower. The other portion of cable extends from the opposite side of the counterweight toward the other end of the table, around the pulley located there, and back toward an attachment to the tower. With this arrangement, motion of the tower in one direction causes an equal amount of motion of the counterweight in the opposite direction. The lengths of the two portions of cable, and the locations of the pulleys, are selected such that the counterweight is directly aligned with the table's pivot axis when the column is also so aligned, and so that the counterweight moves toward one end of the table when the tower is moved toward the opposite end.

An object of this invention is to provide apparatus and method for detecting and indicating the occurrence of excessive strain or failure in a main support of the X-ray table system.

SUMMARY OF THE INVENTION

This invention relates to a method and apparatus for sensing and indicating the occurrence of undesirable strain or failure in a main connector support structure interconnecting components of apparatus such as radiological equipment. An embodiment of the invention includes an auxiliary support structure connected for exerting a force supplementing that exerted by the main supporting structure in an amount which varies as a function of the strain on the main support structure. Such apparatus also includes apparatus for producing a signal in response to a change in the amount of the supplemental force exerted by the auxiliary support structure.

A more specific embodiment of the invention includes safety enhancement apparatus for use in an X-ray table having a movable tower and counterweight coupled for support by a first connector for effecting counterweight movement to adjustably counterbalance the X-ray table when tilted, notwithstanding the tower position. The embodiment comprises a secondary connector coupled substantially in parallel with the main connector for bearing an increased portion of the load between the tower and the counterbalance when strain occurs in the main connector, and means for indicating this increased tension on the secondary connector.

A more specific embodiment of the invention involves detector structure for sensing the increased tension on the secondary connector. This detector structure includes means for deflecting a portion of the secondary connector transversely from its path, so that the deflected portion produces a force component transverse to the path of the secondary connector which is a function of the degree of tension on the secondary connector. A resiliently mounted structure connects the deflected portion of the secondary cable to a limit switch. When the tension on the secondary connector increases to a predetermined extent, the transverse forces produced in the deflected portion of the secondary cable actuate the limit switch, to produce an indication of increased strain in the primary connector.

Because of differing inventorship involved in the system disclosed below, claims of this application have been limited to the general concepts regarding strain detection in radiological equipment, developed by two inventors. Other concepts, relating to interlock circuitry for such equipment were developed by the same two inventors plus one other, and are the subject of the referenced Lutz, et al., application.

These and other features of this invention will become apparent from an examination of the following description and drawings, in which:

A BRIEF DESCRIPTION OF THE DRAWINGS

FIG. 2 is a detailed plan view illustrating a portion of the embodiment of FIG. 1;

FIG. 3 is an elevational view of the structure shown in FIG. 2;

DESCRIPTION OF THE PREFERRED EMBODIMENT

Figure 1:
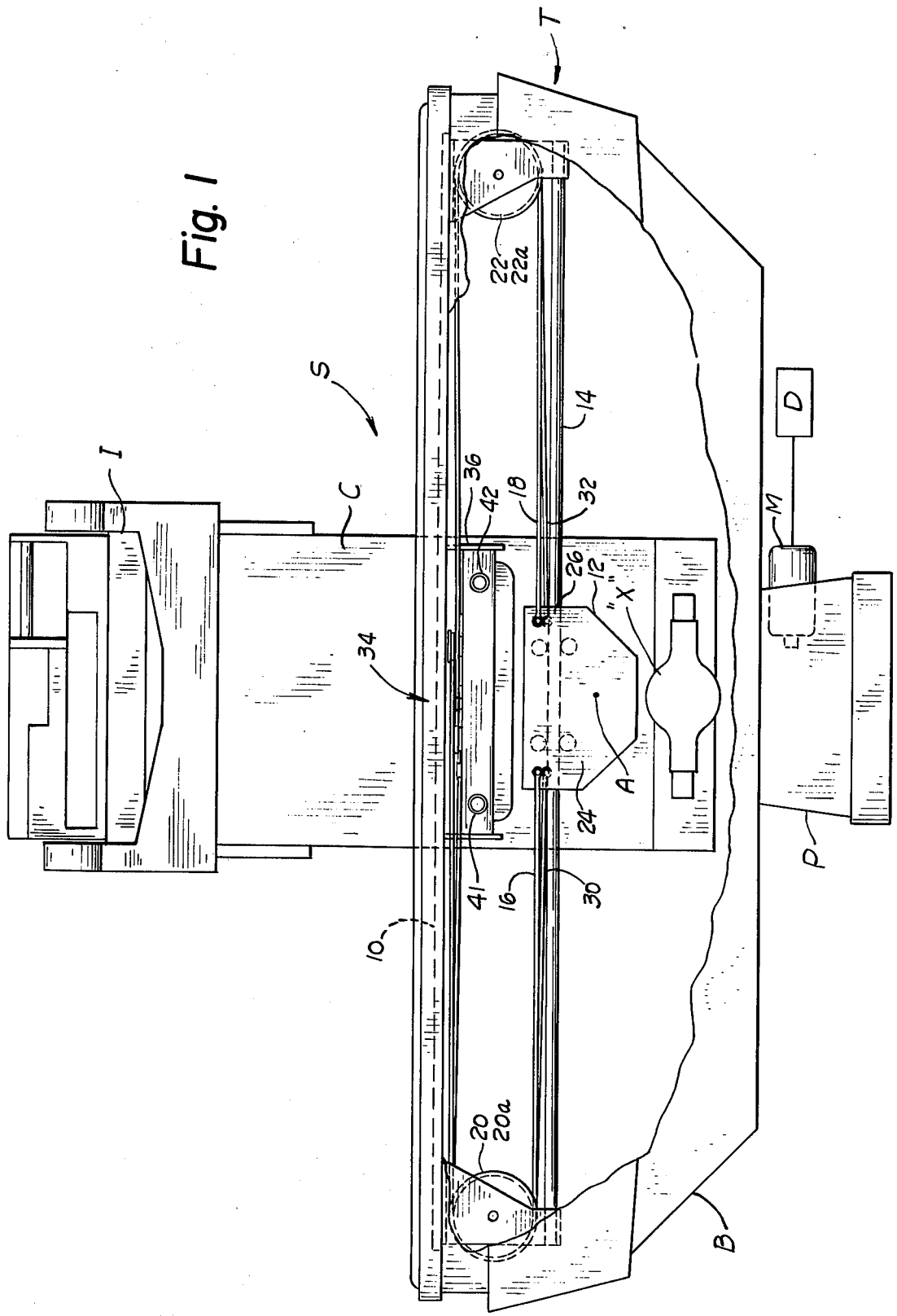
FIG. 1 is an elevational view, partially broken away, illustrating a radiological system incorporating an embodiment of the present invention.

FIG. 1 illustrates a radiological system S incorporating the present invention. The system S directs X-rays through a subject and produces images of the patterns of X-rays emerging from the subject.

The system S includes an X-ray table T for accommodating a subject to be examined, such as a human body. The table T includes a pedestal P and a table body B attached to the pedestal. The system S also includes a tower or column C mounted movably on the table body B which carries the apparatus for making the radiographs. The tower or column C supports an X-ray source X below the top surface of the table T, and also supports an X-ray imaging apparatus I above the top surface of the table T for producing radiographs from patterns of X-rays impinging on the imaging device I after passing from the source X upwardly through the subject.

The X-ray table body B, and the tower or column C mounted on the body, are tiltable, to enable changes in the attitude of the subject during examination. The body B is pivotally mounted on the pedestal P about a pivot axis A. An electric motor M is connected to the table body by way of drive mechanism (not shown) for furnishing the motive power for tilting the table body B. Drive control circuitry D is connected to the motor M for actuating the motor M to pivot the table body B in a desired fashion.

Mechanism is provided for facilitating the motion of the tower C in a direction longitudinal with respect to the table top defined by the table body portion B. The table body B carries a guide track 10 extending longitudinally with respect to the table top along the interior of the table body.

The column C is movable along the longitudinal path defined by the guide track 10. A counterweight 12 is provided for counterbalancing the column C with respect to the table B, irrespective of the position of the column C along the guide track. The counterweight 12 is movably supported in a counterweight track 14 extending along an inside surface of the table body B along a path generally parallel to that of the guide track 10.

The counterweight 12 is connected to the column C by way of two main connector portions 16, 18, which are engaged with a respective pair of connector pulleys 20, 22.

The main connector 16 is fastened to one end 24 of the counterweight 12, is engaged around the connector pulley 20 and is attached to the column C in a manner described below. The main connector portion 18 is fastened to the opposite end 26 of the counterweight 12 and is engaged with the connector pulley 22 and connected to the column C, also in a fashion described below. When the column C is moved to the right as illustrated in FIG. 1, the counterweight 12 moves to the left, in an equal amount, and vice versa. The counterweight C has a weight comparable to that of the column C, with the X-ray source X and the imaging apparatus I mounted thereon.

The X-ray table T is suitably embodied by an X-ray table manufactured by Picker Corporation of Cleveland, Ohio, having the catalog number Series 1240, or Series 1243, and designated by the trade mark "Galaxy." The imaging apparatus I is of known construction, and may suitably be embodied by a spot filmer (referred to above) or by an image intensification device, also known in the art. Likewise, the X-ray source X is of known construction and selectable by one of ordinary skill.

X-rays tables such as illustrated in FIG. 1 differ slightly. One type X-ray table, shown in FIG. 1 specifically, is capable of tilting either clockwise or counterclockwise in any amount up to 90°. Another type of similar X-ray table, such as a Picker Catalog No. Series 1241, or Series 1244, is capable of tilting in a clockwise direction, as viewed in FIG. 1, in any amount up to 90°, and in a counterclockwise direction in any amount up to only about 15°.

Apparatus is provided in the X-ray table T to detect and indicate the occurrence of excessive strain or failure in the main connector portions 16, 18, which may result from overloading or deterioration of these connector portions. This apparatus includes a set of secondary connectors 30, 32 coupling together the counterweight 12 and the column C, to supplement the force exerted by the main connector portions 16, 18, and by detector apparatus 34 for sensing and indicating increases in the forces exerted by the secondary connector portions 30, 32.

The secondary connector portions 30, 32 are respectively connected between the counterweight 12 and the column C by a pair of secondary pulleys 20a, 22a, along paths which are generally parallel to those of the main connector portions 16, 18. Preferably, the secondary connector portions 30, 32 are embodied by woven wire cable having a diameter of approximately 1/8 inch and a tensile strength of approximately 2,000 pounds. Each of the secondary connectors 30, 32 is a length selected such that secondary connectors 30, 32 are stressed to only a relatively small fraction of the stress forces normally exerted on the main connector portions 16, 18.

The detector apparatus 34 includes structure for holding a portion of each of the secondary connectors 30, 32 in a deflected position relative to the general path of the respective secondary connectors. The detector 34 also includes structure for sensing the amount of force transverse to the path of each secondary connector which is exerted by the deflected portion, and which is a function of the amount of tension on the secondary connectors.

If one of the main connectors 16, 18 is stretched, or "strained" by overloading, deterioration, or damage, a portion of the load borne by the main connector is transferred to its associated secondary connector. This increase in tension is sensed by the detector apparatus 34, which produces an indication of that increase, warning of possible strain on the associated main connector.

The detector apparatus 34 includes a detector carriage 36 having mounted therein pulley structure (described below) for deflecting the secondary connectors 30, 32, and a pair of resiliently biased limit switch units 38, 39 (FIG. 2) connected to the deflected portions of the cables for sensing increases in the tension on the associated secondary connectors. The detector carriage 36 also provides anchoring structure for both the main and secondary connectors.

The detector carriage 36 is mounted affixed with respect to the column C by transversely extending carriage structure including a pair of rods 41, 42. The rods 41, 42 each extend transversely across the table body B and are coupled to the column C by suitable structure (not shown) which maintain the rods 41, 42 longitudinally movable with the column C. The detector carriage 36 is integrally connected to the rods 41, 42 and is fixed transversely with respect to the table body B. The detector carriage anchors both the main and secondary connectors 16, 18, 30, 32.

FIGS. 2 and 3 show a detailed embodiment of the detector apparatus 34 employed in connection with the table of FIG. 1. Both the main connectors 16, 18 and the secondary connectors 30, 32 are anchored on the detector carriage 36. The main connector portion 16 is passed over a pulley 44 and anchored at a bolt anchor terminal 46. The end of the main connector 18 attached to the detector carriage 36 is also passed over the pulley 44 and anchored similarly at a bolt anchor terminal 48.

Similarly, the respective ends of the secondary connectors 30, 32 are passed in opposite directions over a pulley 50 and anchored respectively at anchor terminals 52, 54.

The apparatus for deflecting a portion of the secondary connectors 30, 32 is also attached to the detector carriage 36. A portion of the secondary connector 30 is deflected by the combination of a pulley 55, over which the connector is passed, and a pulley 56, attached to the limit switch unit 38. The limit switch unit 38 applies tension to the pulley 56 (upwardly in FIG. 2) which works against the pulley 55 and the pulley 50 to deflect a portion of the secondary connector 30.

In similar fashion, the secondary connector 32 is engaged with and deflected by the coaction of the pulley 50, a pulley 57, and by a pulley 59 attached to the limit switch unit 39.

The limit switch units 38, 39 are substantially identical in construction. Accordingly, only the limit switch unit 38 will be described in detail here, and it will be understood that the construction of the limit switch unit 39 is substantially identical to that of the limit switch unit 38.

The limit switch unit 38 includes a resilient structure 58 having one end fastened to the detector carriage 36, and its other end to the pulley 56. The pulley 56 is rotatably fastened to a plate 61 which is slidably mounted for vertical movement (FIG. 2) on the carriage 36. The resilient structure 58 biases the pulley 56 and plate 61 upwardly in FIG. 2. The plate 61 is connected by suitable connecting structure to one end of a sleeve 63 mounted for axial movement. The sleeve 63 has a tapered portion 67 which actuates a limit switch 60 when the upwardly biased sleeve 63 has been pulled down a predetermined distance by transverse downward forces exerted on the pulley 56 by tension of the secondary connector 30.

Figure 5:
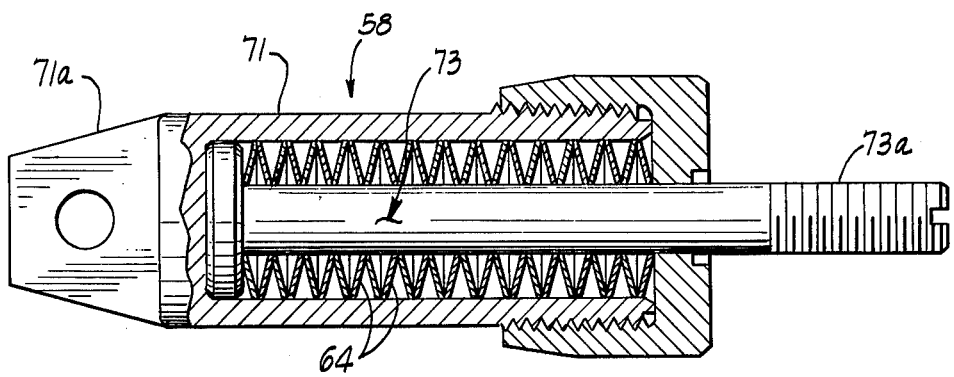
FIG. 5 is a detailed view, partially in cross-section of a portion of the structure shown in FIGS. 2 and 3.

The resilient bias of the structure 58 in an upward direction is obtained by the use of a number of Belleville washers, e.g., 64 (FIG. 5) inserted within a housing 71 of the structure 58 and coaxial with a flanged rod portion 73. The housing 71 is attached to the pulley 56 by a bored flange 71a, and the rod 73 is attached to the carriage 36 by threads 73a.

In operation, if strain occurs in one of the main connectors 16, 18, the lengthening of the affected connector will cause the transfer of at least part of the load borne by the main connector 16 of the associated secondary connector. This occurrence will increase the tension on the secondary connector, and this increased tension will increase the downward force on the pulley component of the associated one of the limit switch units 38, 39. In response to this increased downward force and lessening of the deflection of the secondary connector, the limit switch unit actuates the limit switch 60, which in turn is connected to actuate an audible signal generator 66, such as an electric buzzer or bell, and other circuitry discussed below.

Means is provided for adjusting the operative engagement between the limit switch 60 and the tapered portion 67 of the sleeve 63. The sleeve 63 has an eccentrically-shaped cross-section. The engagement between the tapered sleeve portion 67 and the limit switch 60 is adjustable by rotating the sleeve 63 about a longitudinal axis of the sleeve. This adjustability facilitates compensation for dimensional inaccuracies among the various parts of the detector assembly 34. This feature also enables the adjustment of the predetermined amount of main connector strain and secondary connector tension required to actuate the limit switch 60.

A variant of the X-ray table T, shown in FIG. 1, as discussed above, can tilt in the clockwise direction only to a maximum amount of about 15° from the horizontal. Accordingly, in the variant embodiment, there is no need to provide strain detection features such as discussed above in connection with the main connector 16 and its associated secondary connector 30. This is because the main connector 16 cannot be placed under nearly as much tension as the connector 18.

Accordingly, the detector apparatus used in connection with the variant embodiment of the table T is simpler than that associated with the first discussed embodiment.

Figure 4:
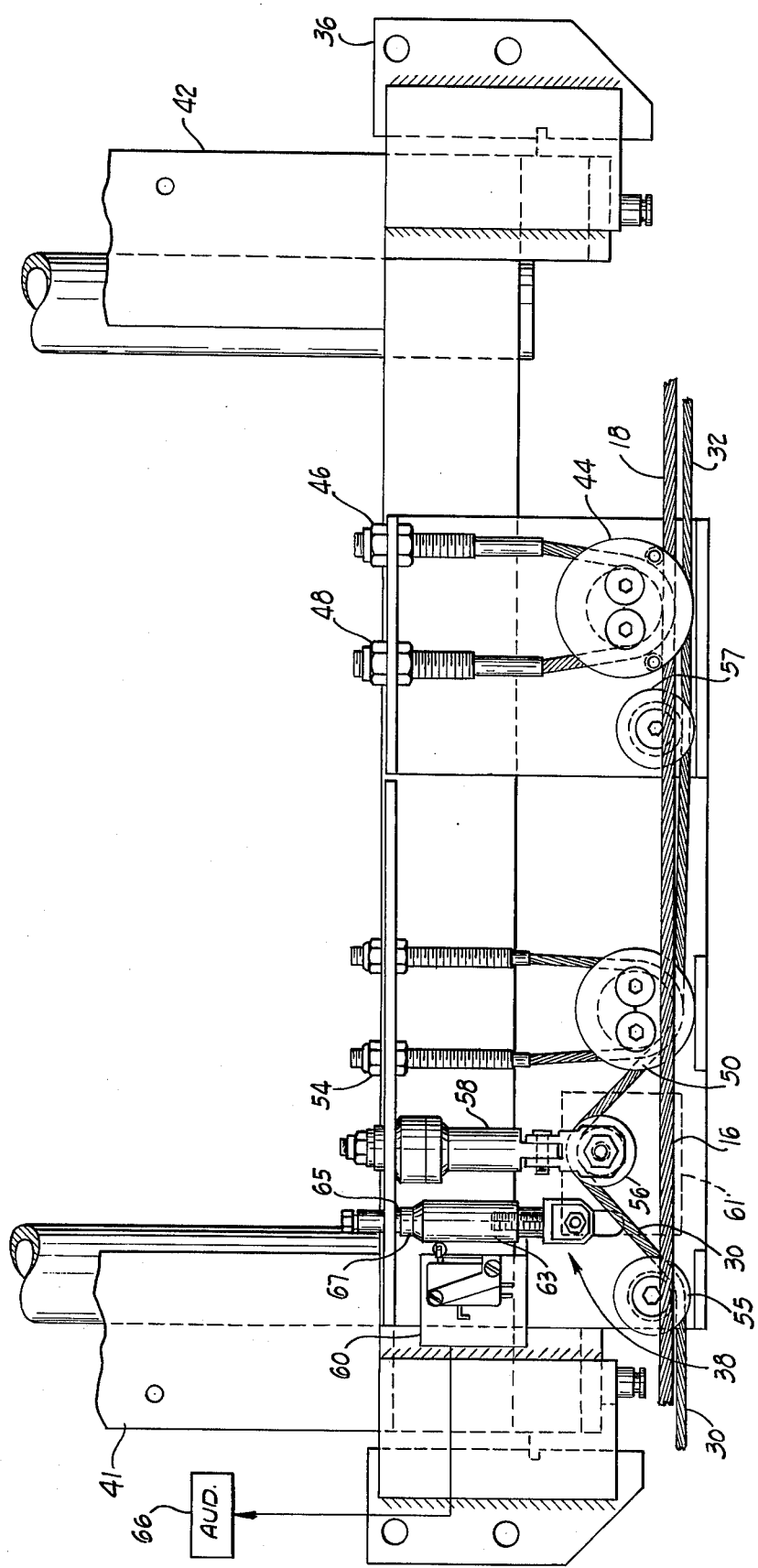
FIG. 4 is a detailed view illustrating another embodiment of the invention incorporated in the structure of FIG. 1.

FIG. 4 shows a slightly different embodiment of the detector apparatus 34 usable in connection with the variant embodiment of the table T, the so-called "90-15" table. Briefly described, the detector apparatus of FIG. 4 substantially identical to that of FIG. 3 except for the exlusion of all the components thereof associated with stress detection in the secondary connector 32. That is, the embodiment shown in FIG. 4 is the same as that of FIG. 3, and operates similarly, with the exception of that the limit switch 39 and the pulleys 59, 57 are omitted.

Figure 6:
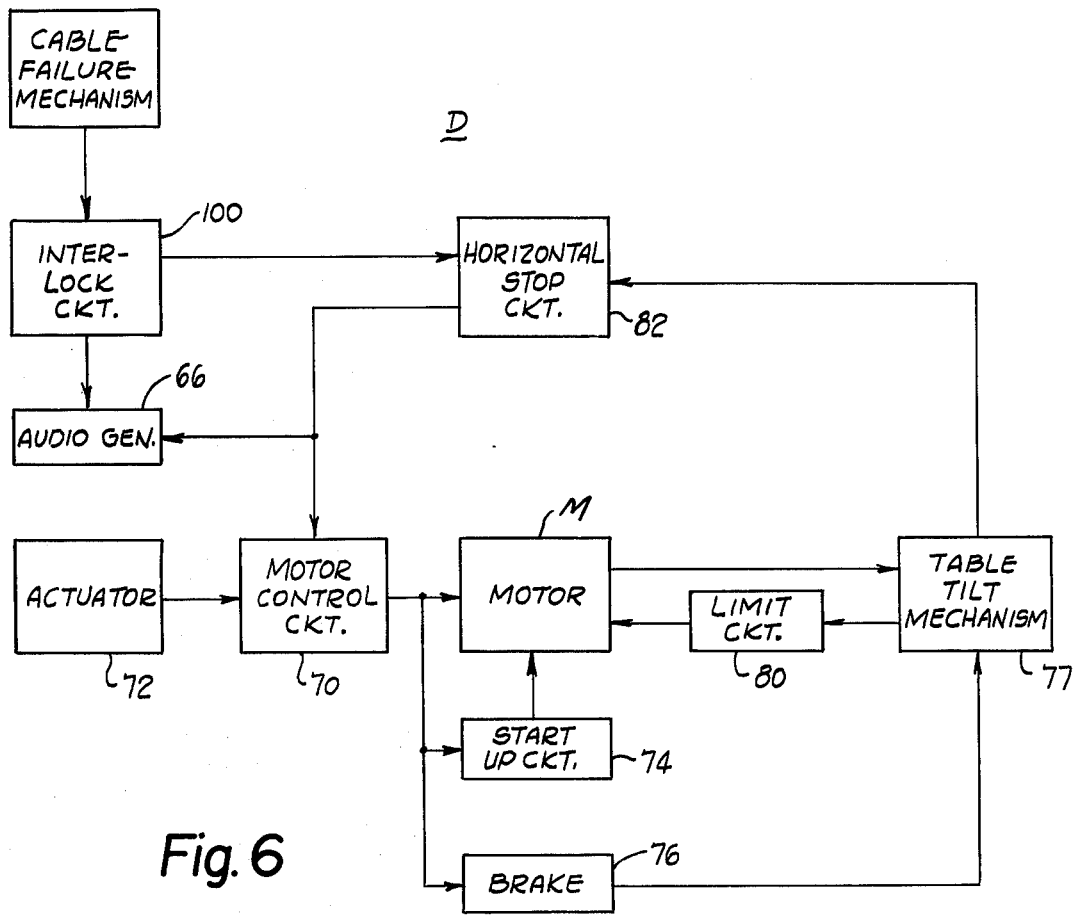
FIG. 6 is a block diagram illustrating a portion of the radiological system shown in FIGS. 1 and 2.

FIG. 6 is a block diagram illustrating the drive control circuitry D and the manner of its connection to the drive motor M. The drive control circuitry D actuates the drive motor M to tilt the X-ray table body B in a predetermined direction and to a predetermined degree. Unless otherwise indicated herein, the components of the drive control circuitry D are of known structure and arrangement, and are embodied in the above-referenced "Galaxy" X-ray tables.

The motor M is suitably embodied by an AC or DC motor having sufficient power to drive the X-ray table body over its desired motion increment. The motor M has armature and field windings connected such that the motor M is reversible, in response to the actuation of certain relay contacts (not shown) connected to the motor M and contained in a motor control component 70.

The relays of the motor control component 70 are actuated to operate the motor M by the depression of an actuator button 72, which is suitably embodied by a switch such as a foot switch operable to selectively close one of two sets of switch contacts for applying power for actuating the motor M to operate in a direction which is determined by which of the switch contacts of the actuator 72 are closed.

The actuator 72, in addition to operating the motor control component 70, operates a start-up circuit 74. The start-up circuit 74 includes circuitry which inserts a removable capacitance (not shown) in the armature windings of the motor M for a predetermined period of time following operation of the actuator button 72, after which the capacitance introduced by the start-up circuit 74 is removed from the armature circuit.

The motor M operates a table tilt mechanism linkage 77 to controllably tilt the table body B in accordance with the speed and duration of operation of the motor M.

A fail-safe mechanical brake 76 (electrically operated) is used to prevent motion of the table body B under any circumstance in which power is not applied to the motor M.

Limiting circuitry 80 responds to the position of the table body B to automatically cut off electric power from the motor M when the table body B has reached a limit of its permitted tilted excursion. The limiting circuitry 80 includes suitable limit switches of known construction coupled to the table tilt mechanism 77 and responsive to sensing the table body B reaching its maximum permitted excursion to disable the motor M from further operation in its immediately previous operating direction.

Horizontal stop circuitry 82, also of known design, responds to the table body B reaching its top-horizontal position to operate upon the motor control circuitry to deactuate the motor M, until a switch contact of the actuator 72 is opened and re-closed. The horizontal stop circuitry 82 is useful in enabling an operator of the table T to return the table body B to its top-horizontal position following tilting to other positions by merely depressing the actuator 72 until the top moves toward the horizontal and stops upon reaching it. This feature eliminates the necessity for "cut and try" methods of returning the table top to the horizontal position.

In operation, the horizontal stop circuitry 82 causes the motor M to stop when the table body B reaches its top-horizontal position after having been rotated from a tilted position. The horiziontal stop circuitry 82, however, does not prevent further operation of the table tilt mechanism 77. It merely serves as a means to halt the table body B at its desired horizontal position. When the actuator 72 is again actuated, the motor M again responds to initiate a new tilting motion of the table body B in the direction corresponding to which of the switch contacts of the actuator 72 is re-closed.

The previously described circuitry of FIG. 6 is, as mentioned above, already known in the art, and therefore has not been described in detail here.

The embodiment of the presently disclosed invention also includes interlock circuitry 100. The interlock circuitry 100 responds to an indication of undesirable strain on one of the main components 16, 18 to disable the motor M to prevent the further tilting of the table body B after it reaches the horizontal position following an indication of such strain. Once the interlock circuitry 100 has disabled the motor M, the table body B cannot again be tilted by operation of the actuator 72 until the strained condition which is indicated has been corrected. Meanwhile, however, the other components of the X-ray table T remain fully operable, insofar aas they can be used for the examination of subjects with the table top in its horizontal position.

Figure 7:
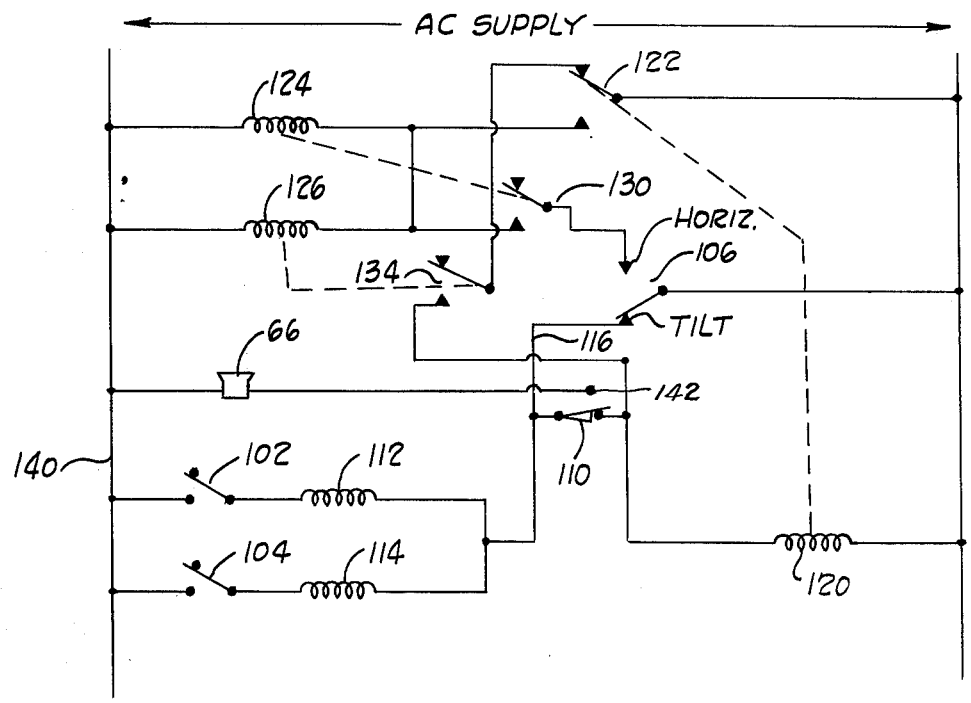
FIG. 7 is a schematic drawing of a portion of the system shown in FIG. 6.

FIG. 7 is a schematic diagram illustrating one embodiment of the interlock circuitry 100. The interlock circuitry 100 performs two functions. First, it responds to the sensing of a strained condition of predetermined magnitude in one of the main connectors 16, 18 to prevent the table body B from being further tilted after the table body has been returned to its horizontal position. Second, the interlock circuitry 100 actuates the audio signal generator 66 to emit a warming signal constantly until the table body B is returned to its top-horizontal position after the sensing of the strained main connector.

The lockout circuitry 100 operates in response to a pair of actuator switches 102, 104, the position of a level control switch 106, and the condition of a detector switch 110. The switches 102, 104 are normally open switches, which can be separately closed by actuation of the actuator 72. The level control switch 106 constituting a portion of the horizontal stop circuitry 82. The level control switch contacts its upper terminal, as shown in FIG. 7, when the table top of the body B is in a horizontal position. At all other times, the level switch contacts its lower contact. The detector switch 110 is normally in contact with its lower terminal, as viewed in FIG. 7, but, in response to the sensing of a strained condition in a main connector, moves to contact its upper terminal. The detector switch 110 is responsive to the actuation of one of the limit switches 60 in connection with one of the limit switch units 38, 39.

The switches 102, 104 are connected in series with one of two operation relays 112, 114, respectively, which constitute part of the motor control circuitry 70. The operation relay 112 actuates relay contacts (not shown) which actuate the motor M to operate in one direction. Actuation of the operation relay 114 actuates a set of relay contacts associated with the motor M to cause the motor M to operate in the other direction.

When the switch 102 is closed, for example, by operation of the actuator 72, the relay 112 is actuated, causing the motor M to tilt the table body B in a predetermined direction. If the table body B is already tilted, the switch 106 will contact its lower terminal, and normally the switch 110 will contact its lower terminal.

Under these conditions (no strain detection and table body B tilted), current is shunted around the switch 110 through a lead 116 and through the switch 106, and the table body B is tilted by operation of the motor M.

When the table body B has tilted enough to bring the table top to a horizontal position, the switch 106 moves to contact its upper terminal. Current can no longer flow through the lead 116, and current therefore flows through the switch 110 and through a lockout relay 120. Energization of the lockout relay 120 reduces voltage to the relays 112, 114 to a degree sufficient to deactuate these relays and cut off power from the motor M, while the relay 120 is energized.

The lockout relay 120 moves a relay contact 122 to contact its lower terminals as viewed in FIG. 7, which in turn causes the actuation of a latching relay 124 and a bypass relay 126. Actuation of the latching relay 124 closes a normally-open relay contact 130 which latches in the relays 124, 126, by virtue of the fact that the switch 106 contacts its upper terminal in this condition.

This condition, in which the lockout relay 120 is actuated, halts the tilting operation of the table body B as the table body is tilted through the horizontal. Under normal circumstances, however, the deactuation and reactuation of the actuator 72 causes the immediate resumption of tilting motion of the table body B. This resumption of motion is enabled by bypass circuitry in the interlock circuitry of FIG. 7.

The bypass circuitry includes the bypass relay 126 and a normally-open relay contact 134. After the table body B has reached its top-horizontal position and the closed one of the switches 102, 104 is released, opening the switch, the application of power to the lockout relay 120 ceases, and the contact 122 resumes its normal condition, i.e., it contacts its upper terminal. Since the bypass relay 126 is actuated, the normally-open contact 134 is closed, furnishing a current path from the right-hand end of the switch 110, through the contact 134 and 122. Thus, when one of the switches 102, 104 is reclosed, the current flowing through the associated relay 112, 114, rather than being directed through the lockout relay 120, is simply shunted through the contacts 134, 122. This enables the continued tilting operation of the table body B.

The above discussion in connection with FIG. 7 has assumed that the switch 110 was closed, which is the case when no excessive main connector strain has been detected. In instances in which excessive strain has been detected, the switch 110 is opened in response to actuation of one of the limit switch units 37, 39. The opening of the switch 110 disables the effect of actuation of the bypass relay 126, by cutting off current flow through the contacts 134, 122.

Under these conditions, the operation of the system prior to the table body B reaching its top-horizontal position is the same as described above. Under such conditions, when one of the switches 102, 104 is closed, while the body B is n a nonhorizontal position, the current flowing through the associated relay 112, 114 is shunted to ground by way of the switch 106 and the lead 116, until the table reaches its horizontal position. At that point, the switch 106 changes its position to contact its upper terminal.

From this point on, operation of the circuit with the switch 110 in its open condition is different from that described above. In this condition, the bypass circuitry including the contacts 134, 122 are rendered ineffective, and it becomes impossible to actuate the motor M to operate the table further until the detected cable strain condition is corrected, closing the switch 110. The opening and re-closing of one of the switches 102, 104 thus has no effect on the operation of the system. This is true because the open switch 110 prevents current from flowing from the relays 112, 114 through the contacts 134, 122 when the switches 102, 104 are opened and re-closed.

The circuitry of FIG. 7 also actuates the audio signal generator 66 to produce an audio signal indicating cable strain when the switch 110 is opened. The production of this signal continues through the entire time subsequent to the opening of the switch 106 in which the table body B continues in a nonhorizontal position, and the audio signal generation ceases only when the table has reached a horizontal position. The audio signal generator 66 is shown in FIG. 7 as connected between the electrical lead 140, serving as a power source, and an upper terminal 142 of the switch 110. The common of the switch 110 is connected to the lead 116.

When the switch 110 is closed, no current can flow through the audio generator 66. When the switch 110 is opened, however, the connection to the upper terminal 142 furnishes a current path to the audio generator 66 through the lead 116 and to the switch 106, as long as the table body B is in a tilted position. When, however, the table body B reaches the horizontal position, the switch 106 contacts its upper terminal, breaking the connection between the lead 116 and ground, which causes the audio generator to cease its signal generation.

Figure 8:
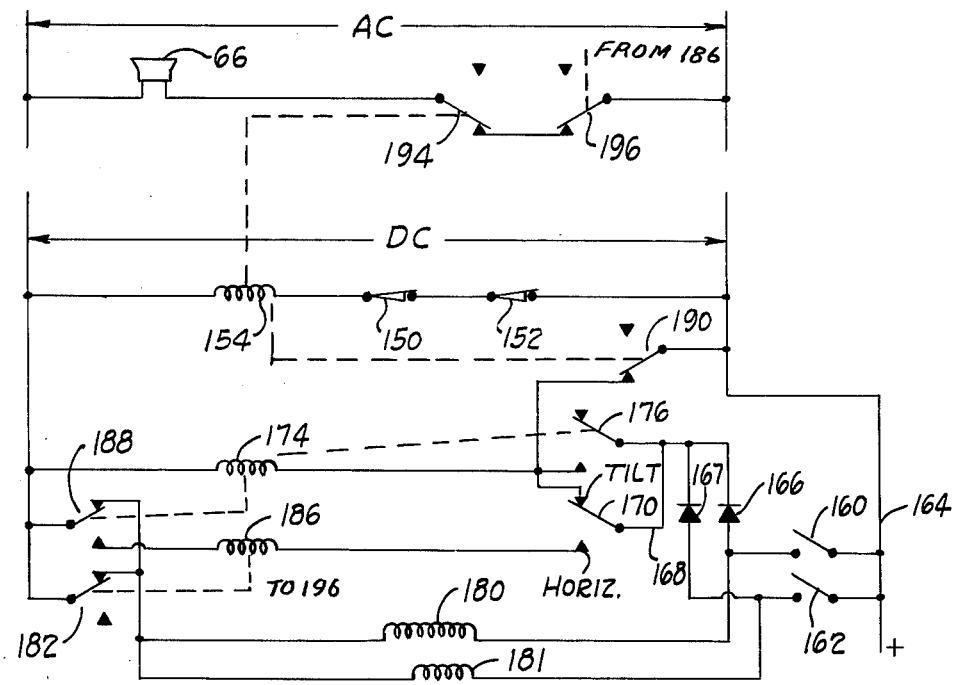
FIG. 8 is a schematic drawing of another embodiment of that portion of the system shown in FIG. 7.

FIG. 8 shows an alternate embodiment for the relay circuitry for accomplishing the analogous functions as are accomplished by the circuitry of FIG. 7, in connection with the so-called "90—90 degree" X-ray table. This table, as explained above, has two auxiliary connectors 30, 32 and two limit switch units 38, 39. The switches actuated by the limit switch units 38, 39 are illustrated in FIG. 8 as switches 150, 152. Each of these switches remains closed in the absence of an excessive strain detection, and each switch opens in response to the detection of a strained condition in its associated secondary connector. As long as these switches 150, 152 are closed, a relay 154 is energized. The relay 154 is connected to a series of contacts (not shown) which enable the operation of the motor M to operate the tiltable table body B. The relay 154 is thus energized under normal operating conditions in which there is no connector failure.

FIG. 8 also shows a set of switches 160, 162 which correspond to the switches 102, 104 in the previously discussed figure. When one of the switches 160, 162 is closed, by actuation of the switch actuator 72, a current path is provided from a lead 164 through one of the isolation diodes 166, 167 and a lead 168. The operative effects of the switches 160, 162 are analogous, and only the operation of the switch 160 is discussed here, for purposes of simplicity.

The lead 168 is connected to a level switch 170 which is analogous to the level switch 106 in the previous figure. The level switch 170 contacts its upper terminal in conditions in which the table body B is in a nontop-horizontal position, and contacts its lower terminal when the top reaches a horizontal position. Thus, when the switch 160 is closed a current path is provided through the level switch 170 actuating a relay 174. Actuation of the relay 174 closes a normally-open latching contact 176, which enables the actuation of the relay 174 for as long as one of the switches 160, 162 is closed, even after the switch 170 has moved to contact its lower terminal in response to the reaching of a horizontal position by the table top of the body B.

Also, when the switch 160 is closed, power flows through an actuating relay 180 which is connected to relay contacts associated with the motor M causing the motor M to operate to tilt the table top. A current path through the relay 180 is furnished by a normally-closed relay contact 182 associated with the relay 186 or a relay contact 188 associated with the relay 174.

When the table top reaches its horizontal position, the switch 170 contacts its lower terminal. Since the latching relay contact 176 is closed by operation of the relay 174, the current path through the relay 174 remains unbroken, and this relay remains in its actuated condition for as long as the closed one of the switches 160, 162 continues to be closed. The current path through the switch 170, however, is interrupted.

When the switch 170 moves to contact its lower terminal in response to the table top reaching the horizontal position, a relay 186 is actuated by a current passing through a normally-open contact 188 (which is held in its closed condition by actuation of the relay 174). Actuation of the relay 186 causes the opening of the normally-closed contact 182, thus cutting off power from the actuating relay 180, and causing the motor M to halt its operation.

When one of the switches 160, 162 is then opened and re-closed, the motor M is actuated by the relay 180, 181 to resume tilting motion of the table body B. When the closed one of the switches 160, 162 is opened, the relay 174 becomes deactuated. The latching relay contact 176 opens and the contact 188 moves to contact its upper terminal. Since the relay 186 is deactuated, the normally-closed contact 182 returns to its upper terminal. The movement of the contact 188 to contact its upper terminal again furnishes a current path through the actuation relay 180 such that, when the switch 160 is re-closed, power flows through the relay 180 and the motor M is actuated to tilt the table body B away from the horizontal.

Operation of the system is different when a strained condition is sensed, and one of the switches 150, 152 is opened, deactuating the relay 154. When the relay 154 is deactuated, a normally-open relay contact 190 (held open by energization of the relay 154) is caused to move to its normally-closed condition.

If the table body B is in a tilted position, and the switch 170 contacts its upper terminal, closure of the switch 160 causes current flow through the relay 174, actuating the contact 176 to close. Power for actuating the operation relay 180 flows from the closed switch 160 through the relay 180 and the normally-closed contact 182. When, however, the table body B reaches its top-horizontal position, the switch 170 moves to contact its lower terminal, actuating the relay 186. Actuation of the relay 186 opens the normally-closed contact 182, interrupting the current path through the relay 180, causing the motor M to become deactuated, and unable to tilt the table body any further.

Under these conditions, the opening and re-closure of one of the switches 160, 162 does not effect the continued motion of the table body B, as in the case of the previous example.

The earlier deactuation of the relay 154 causes the closing of the normally-closed relay 190. The closure of this relay 190 assures that the relay 174 will be continuously actuated from that time on. This actuation closes the latching relay contact 176, and also moves the relay contact 188 to contact its lower terminal causing the actuation of the relay 186. The relay 186 causes the opening of the normally-closed contact 182, such that even if the switch 160 is re-closed, there is no path for current to flow through the operation relay 180. Thus, when a strained condition is detected, the circuitry of FIG. 8 entirely disables the motor M from operation, when the top-horizontal position is attained, until the strained condition is corrected, causing the closure of the opened one of the switches 150, 152.

As in the case of FIG. 7, the existence of a strained condition causes the actuation of the audio generator 66, as long as the table body B has its top in a nonhorizontal tilted position. The production of the signal generated by the generator 66 ceases only when the table top is returned to a horizontal position.

It has been seen, from the discussion above, that the relay 154 is actuated during any condition in which there is no strain detected and deactuated when a strain is detected. The relay contact 194 is a normally-closed contact which is maintained in its open condition as long as the relay 154 is actuated, as during normal unstrained operation.

Additionally, a relay contact 196 is provided which is normally-closed, and which is opened in response to actuation of the relay 186. As has been seen from the above discussion, the relay 186 is actuated only when the top of the table body B is in a horizontal position. Thus, the audio generator 66 is actuated whenever the following two conditions prevail: (1) the relay 154 is deactuated indicating a strained condition in one of the secondary connectors; and (2) the relay 186 is not actuated, indicating that the table top of the body B is in a nonhorizontal position. When the table body B reaches a horizontal position the relay 186 is actuated, thus opening the contact 196 and ceasing operation of the audio signal generator 66.

It is to be understood that the above description is intended as illustrative rather than exhaustive of the invention. Those of ordinary skill in the art may make certain adaptations, changes, or modifications to the invention as disclosed here without departing from the spirit of the invention or the scope of the appended claims.

What is claimed is:

1. Apparatus for detecting stress in a primary support structure for exerting primary force for supporting a component of medical diagnostic equipment, said apparatus comprising:
   a. an auxiliary support structure connected to said component for independently exerting force on the component for supplementing the primary supporting force of the primary support structure in an amount which varies in response to the occurrence of strain in said primary support structure; and,
   b. apparatus for producing a signal in response to a change in the amount of said supplemental force exerted by said auxiliary support structure.

2. The apparatus of claim 1, further comprising: apparatus responsive to said change in supplemental force exertion for restricting a subsequent operation of said radiological equipment.

3. Safety enhancement apparatus for use in an X-ray table having a movable tower for supporting radiological apparatus and a counterweight coupled to the tower by a first connector under tension for effecting counterweight movement for adjustably counterbalancing the X-ray table with respect to the position of the tower, said safety apparatus comprising:
   a. a secondary connector coupled substantially in parallel with said first connector for bearing an increased portion of the tension load between the tower and the counterweight when strain occurs in the first connector; and,
   b. means for indicating said increased tension on said secondary connector.

4. Apparatus for detecting strain in a primary support structure for a component of a radiological system, the primary support structure including two first connectors connected to the component, said apparatus comprising:
   a. two secondary support structures each comprising a second connector connected in parallel with a different one of said two first connectors; and,
   b. apparatus for separately detecting a predetermined variation in the amount of force exerted on the component by each of the second connectors and for producing a signal in response to the occurrence of said predetermined variation.

5. Apparatus for detecting stress in a primary structure for exerting primary force for supporting a component of mechanized equipment, said apparatus comprising:
   a. an auxiliary support structure connected for independently exerting force supplementing the primary supporting force of the primary support structure in an amount which varies in response to the occurrence of strain in said primary support structure; and,
   b. apparatus for producing a signal in response to a change in the amount of said supplemental force exerted by said auxiliary support structure.

6. Apparatus for detecting stress in a primary support structure for exerting primary force for supporting a component of radiological equipment, the primary support structure including a cable connected to said component, said apparatus comprising:
   a. an auxiliary support structure including a different cable connected to said component and extending along a path substantially parallel to that of the primary support cable structure, said auxiliary support cable structure being connected for exerting force supplementing the primary supporting force of the primary support cable structure in an amount which varies in response to the occurrence of strain in said primary support cable structure; and
   b. apparatus for producing a signal in response to a change in the amount of said supplemental force exerted by said auxiliary support structure.

7. Safety enhancement apparatus for use in an x-ray table having a movable tower for supporting radiological apparatus and a counterweight coupled to the tower by a first connector under tension for effecting counterweight movement for adjustably counterbalancing the x-ray table with respect to the position of the tower, and safety apparatus comprising:
   a. a secondary connector coupled substantially in parallel with said first connector for bearing an increased portion of the tension load between the tower and the counterweight when the strain occurs in the first connector; and
   b. apparatus for indicating said increased tension on said secondary connector comprising:
      i. structure engaged with the secondary connector for deflecting a portion of the secondary connector so that increased tension on said secondary connector produces forces in its deflected portion transverse to the path of said secondary connector through said deflected portion;
      ii. an electrical switch coupled to sense the occurrence of said transverse forces on said secondary connector;
      iii. a second deflector means for deflecting a second portion of said second secondary connector so that increased tension on said secondary connector in said second deflected portion produces forces transverse to the extension of the second deflected portion, and
      iv. a second electrical switch coupled to sense said increased tension in said second deflected portion.

8. Safety enhancement apparatus for use in an x-ray table having a movable tower for supporting radiological apparatus and a counterweight coupled to the tower by a first connector under tension for effecting counterweight movement for adjustably counterbalancing the x-ray table with respect to the position of the tower, said safety apparatus comprising:
   a. a secondary connector coupled substantially in parallel with said first connector for bearing an increased portion of the tension load between the tower and the counterweight when strain occurs in the first connector, and
   b. means for indicating said increased tension on said secondary connector, said tension indicating means comprising:
      i. structure engaged with the secondary connector for deflecting a portion of the secondary connector so that increased tension on said secondary connector produces forces on its deflected portion transverse to the path of said secondary connector through said deflected portion, and ii. an electrical switch coupled to sense the occurrence of said transverse forces on said secondary connector.

9. The apparatus of claim 15, wherein said deflecting means comprises:
   a pulley guide structure engaged with said secondary connector, and
   b. a spring actuated microswitch coupled to said deflected portion for producing an indication of the occurrence of said transverse forces in response to a predetermined extension of said spring.

10. Safety enhancement apparatus for use in an x-ray table having a movable tower for supporting radiological apparatus and a counterweight coupled to the tower by a first cable connector under tension for effecting counterweight movement for adjustably counterbalancing the x-ray table with respect to the position of the tower, said safety apparatus comprising:
   a. a secondary cable connector being of lighter gauge than said first cable connector coupled substantially in parallel with said first cable connector for bearing an increased portion of the tension load between the tower and the counterweight when strain occurs in the first connector, and
   b. means for indicating said increased tension on said secondary connector.

11. Apparatus for detecting stress in a primary support structure for exerting primary force for supporting a component of medical diagnostic equipment, said apparatus comprising:
   a. a single cable auxiliary support structure connected for exerting force supplementing the primary supporting force of the primary support structure in an amount which varies in response to the occurrence of strain in said primary support structure, said auxiliary support structure being connected and constructed to be capable of exerting sufficient supplemental force to support said component independently, and
   b. apparatus for producing a signal in response to a change in the amount of said supplemental force exerted by said auxiliary support structure.

12. The apparatus of claim 11, further comprising:
   apparatus responsive to said change in supplemental force exertion for restricting a subsequent operation of said radiological equipment.

13. A medical diagnostic system comprising:
   a. an x-ray table tiltable about a horizontal axis perpendicular to its length;
   b. a tower mounted on the table for movement longitudinally along the table;
   c. an x-ray source on the tower for directing x-rays through a subject on the table;
   d. a counterweight movably mounted to the table;
   e. primary and secondary support cables connecting the counterweight and the tower for coordinating movement therebetween wherein the counterweight facilitates balance of the tiltable table about its axis notwithstanding movement of the tower;
      i. said primary support cable being for exerting a primary support force between the counterweight and the tower;
      ii. said secondary cable being connected directly between the counterweight and tower for exerting independently a supplemental force which varies in response to the occurrence of strain in the primary cable, and
      iii. apparatus for restricting the tilting of the table in response to the exertion of a predetermined amount of supplemental force by the secondary cable.

14. Apparatus for supporting a suspended load, comprising:
   a. a primary cable connected for supporting the load;
   b. a secondary cable connected to the load independently of other support cables, said secondary cable supplying a supplemental supporting force which is a function of the amount of strain in the primary cable, and
   c. apparatus responsive to the exertion of a predetermined amount of supplemental force by the secondary cable to produce a warning signal.

* * * * *

UNITED STATES PATENT OFFICE
CERTIFICATE OF CORRECTION

Patent No. 4,064,500      Dated December 20, 1977

Inventor(s) Henry R. Sokol et al.

It is certified that error appears in the above-identified patent and that said Letters Patent are hereby corrected as shown below:

Column 3, line 7, delete "counterbalance" substitute -- counterweight --.

Column 4, line 14, "furnising" should be -- furnishing --.

Column 7, line 20, after "FIG. 4" insert -- is --; line 21, "exlusion" should be -- exclusion --; line 25, delete "of".

Column 8, line 40, delete "components" substitute -- connectors --; line 48, "aas" should be -- as --; line 59, "warming" should be -- warning --.

Column 9, line 40, "terminals" should be -- terminal --.

Column 10, line 8, delete "37" substitute -- 38 --; line 16, delete "n" substitute -- in --; line 38, change "through" to -- throughout --.

Column 15, line 7, after "a" insert -- . --.

Signed and Sealed this

Twenty-fifth Day of April 1978

[SEAL]

Attest:

RUTH C. MASON      LUTRELLE F. PARKER
Attesting Officer      Acting Commissioner of Patents and Trademarks